United States Patent
Rice et al.

(10) Patent No.: US 9,411,823 B1
(45) Date of Patent: Aug. 9, 2016

(54) HANDHELD MEDICAL IMAGING MOBILE MODALITY

(71) Applicant: Mach 7 Technologies, Inc., Colchester, VT (US)

(72) Inventors: Eric Rice, Panton, VT (US); Alexey V. Ulanov, Williston, VT (US); Martin Stefanov, South Burlington, VT (US)

(73) Assignee: Mach 7 Technologies, Inc., South Burlington, VT (US)

( * ) Notice: Subject to any disclaimer, the term of this patent is extended or adjusted under 35 U.S.C. 154(b) by 0 days.

(21) Appl. No.: 13/840,561

(22) Filed: Mar. 15, 2013

Related U.S. Application Data

(60) Provisional application No. 61/729,572, filed on Nov. 24, 2012.

(51) Int. Cl.
*G06F 3/12* (2006.01)
*G06F 17/30* (2006.01)
*G06F 19/00* (2011.01)

(52) U.S. Cl.
CPC ........ *G06F 17/30244* (2013.01); *G06F 19/322* (2013.01)

(58) Field of Classification Search
USPC .................... 358/1.6, 1.15, 403; 705/2, 3, 55; 455/556.1
See application file for complete search history.

(56) References Cited

U.S. PATENT DOCUMENTS

| | | | |
|---|---|---|---|
| 7,613,620 B2 * | 11/2009 | Salwan | 705/2 |
| 2002/0049684 A1 * | 4/2002 | Nagamoto et al. | 706/1 |
| 2008/0021730 A1 | 1/2008 | Holla | |
| 2008/0146277 A1 * | 6/2008 | Anglin et al. | 455/556.1 |
| 2009/0012878 A1 | 1/2009 | Tedesco | |
| 2009/0080742 A1 * | 3/2009 | Moriya | 382/131 |
| 2009/0087047 A1 * | 4/2009 | Moriya | 382/128 |
| 2009/0150292 A1 * | 6/2009 | Trinh et al. | 705/55 |
| 2009/0256701 A1 * | 10/2009 | Chamberlain et al. | 340/539.12 |
| 2009/0259490 A1 * | 10/2009 | Colang et al. | 705/3 |
| 2009/0284486 A1 * | 11/2009 | Albus | 345/173 |
| 2009/0310843 A1 * | 12/2009 | Moriya | 382/131 |

(Continued)

OTHER PUBLICATIONS

Hassan M. Bassiouni, "Phonoarthrography: A New Technique for Recording Joint Sounds," Chapter 16 in book, Osteoarthritis—Diagnosis, Treatment and Surgery Source: InTech, Mar. 2, 2012, available at http://www.intechopen.com/books/statistics/osteoarthritis-diagnosis-treatment-and-surgery/phonoarthrography-a-new-technique-for-recording-joint-sounds.

*Primary Examiner* — Kimberly A Williams
(74) *Attorney, Agent, or Firm* — James Marc Leas

(57) ABSTRACT

A method of acquiring medical image data for a subject having a subject medical record and subject identifying information includes capturing medical image data related to the subject with a mobile wireless-communication optical-imaging device. The mobile wireless-communication optical-imaging device includes an optical imaging component, an input component, and a wireless two-way communication component. The method also includes providing a program that includes a program includes a request for subject identifying information, providing the subject identifying information in said program, and wirelessly transmitting data derived from the medical image data and the subject identifying information from the mobile wireless-communication optical-imaging device to a second device. The second device is separate from the mobile wireless-communication optical-imaging device.

30 Claims, 5 Drawing Sheets

(56) References Cited

U.S. PATENT DOCUMENTS

| | | | |
|---|---|---|---|
| 2010/0067706 A1* | 3/2010 | Anan et al. | 380/285 |
| 2011/0029326 A1* | 2/2011 | Venon | 705/3 |
| 2012/0041782 A1* | 2/2012 | Morris | 705/3 |
| 2012/0065995 A1* | 3/2012 | Singh et al. | 705/3 |
| 2012/0173278 A1* | 7/2012 | Herbst et al. | 705/3 |
| 2012/0185267 A1* | 7/2012 | Kamen et al. | 705/2 |
| 2012/0221353 A1* | 8/2012 | Dvorak et al. | 705/3 |
| 2012/0233000 A1 | 9/2012 | Fisher | |
| 2013/0013331 A1 | 1/2013 | Horseman | |
| 2013/0031232 A1* | 1/2013 | Clymer et al. | 709/223 |
| 2013/0090938 A1* | 4/2013 | Fishman et al. | 705/2 |
| 2013/0132109 A1* | 5/2013 | Mruthyunjaya et al. | 705/2 |
| 2013/0179185 A1* | 7/2013 | Duffy et al. | 705/3 |
| 2013/0185331 A1* | 7/2013 | Conemac | G06F 19/321 707/783 |
| 2013/0282400 A1* | 10/2013 | Al-Moosawi | 705/3 |
| 2013/0298082 A1* | 11/2013 | Soffer | G06F 3/0482 715/835 |
| 2014/0006055 A1* | 1/2014 | Seraly et al. | 705/3 |
| 2014/0058751 A1* | 2/2014 | Eaves et al. | 705/3 |
| 2014/0122109 A1* | 5/2014 | Ghanbari et al. | 705/2 |
| 2014/0122125 A1* | 5/2014 | Deshpande | G06F 19/3418 705/3 |
| 2014/0155760 A1* | 6/2014 | Ridder et al. | 600/479 |
| 2014/0156302 A1* | 6/2014 | Larsen | 705/2 |
| 2014/0304638 A1* | 10/2014 | Yoshikawa et al. | 715/771 |

* cited by examiner

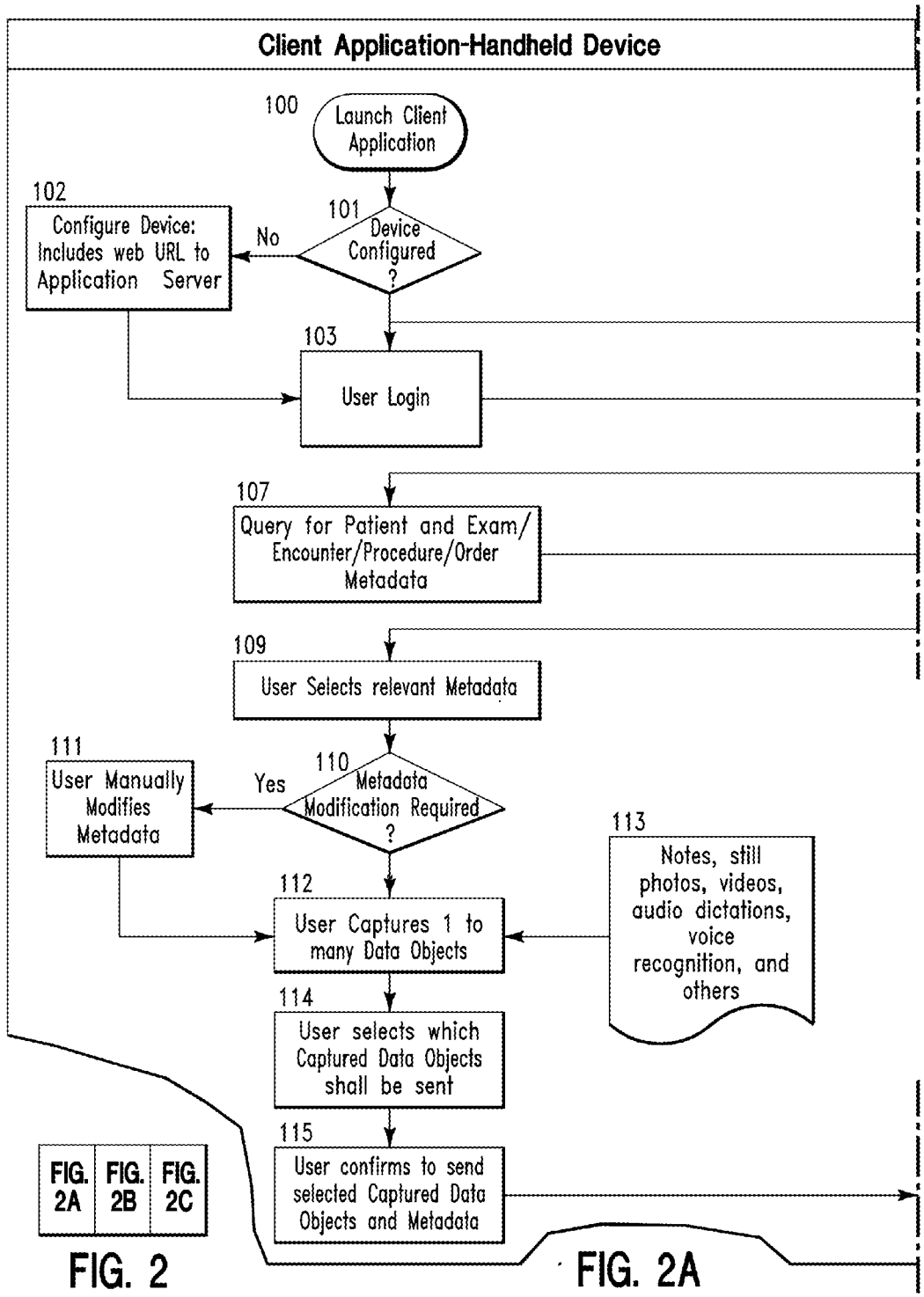

HANDHELD MEDICAL IMAGING MOBILE MODALITY

FIELD

This patent application generally relates to a system for obtaining and transferring images to a subject medical record. More particularly, it relates to a system that uses a handheld mobile imaging and communications device to capture an image and transfer the image to the identified subject medical record on a server.

BACKGROUND

During examination or self-examination, medical providers and patients make observations that they might like to image and record in the patient's medical record if a convenient scheme to do so was available. 60% of medical imaging data is captured outside of the well-established digital imaging departments of Radiology and Cardiology. Examples include moles and rashes in Dermatology, lesions within Wound Care, abuse cases, surgical procedures, varicose vein treatments, diabetic ulcers, and more. Outside of Radiology and Cardiology, medical facilities struggle in optimizing workflow to capture medical imaging data digitally and to store and share the data on a patient's electronic medical record in an electronic medical record system. Often the digital photographs are printed and stored in locked cabinets and the photographs are lost to future clinical reference.

In certain existing systems, a user loads photographs and/or videos from a camera to a computer, then finds each photograph or video on the computer, associates it with a patient or an exam, and uploads to that patient's medical record. This process, has been time consuming and requires substantial user coordination between the camera, the computer, and the electronic medical record system.

Applicants recognized that better schemes are needed to simplify the process of capturing and storing medical imaging data, including medically related photographs and video, and such solutions are provided by the following description.

SUMMARY

One aspect of the present patent application is a method of acquiring medical image data for a subject having a subject medical record and subject identifying information. The method includes capturing medical image data related to the subject with a mobile wireless-communication optical-imaging device. The mobile wireless-communication optical-imaging device includes an optical imaging component, an input component, and a wireless two-way communication component. The method also includes providing a program that includes a request for subject identifying information, providing the subject identifying information in said program, and wirelessly transmitting data derived from the medical image data and the subject identifying information from the mobile wireless-communication optical-imaging device to a second device. The second device is separate from the mobile wireless-communication optical-imaging device.

Another aspect is a method of capturing medical data of a subject by a user. The method includes providing a wireless communications digital server system, wherein the wireless communications digital server system is capable of wirelessly receiving and transmitting digital data. The wireless communications digital server system includes a memory with a medical record data base that includes a medical record for the subject. The method also includes providing a mobile wireless-communications optical-imaging device, that includes an imaging component and a communications component. The imaging component is capable of acquiring a digital optical image and the communications component is capable of wirelessly receiving and transmitting digital data. The method also includes acquiring authenticating information of the user with the mobile wireless-communications optical-imaging device and transmitting the authenticating information to the wireless communications digital server system, acquiring identifying information of the subject, acquiring a medical digital image of the subject with the imaging component, acquiring the subject identifying information, transmitting data derived from the subject identifying information and the medical digital image, and receiving the transmitted data with the wireless communications digital server system.

Another aspect is a method of providing medical image data associated with the subject's medical record identification. The method includes providing a mobile wireless-communication optical-imaging device that includes an optical imaging device, an input device, and a wireless two-way communication device. The method also includes acquiring medical image data related to the subject with the mobile wireless communication imaging device, providing the subject identifying information, and wirelessly transmitting data derived from the medical image data and the subject identifying information with the mobile wireless-communication optical-imaging device to a device used for at least one from the group consisting of display, communicate, and store health care information and subject diagnosis, prevention, and treatment.

Another aspect is a method of providing medical image data associated with a subject's medical record identification. The method includes acquiring medical image data related to the subject with a mobile wireless-communication optical-imaging device that includes an input component, an optical imaging component, and a wireless two-way communication component. The method also includes providing the subject identifying information to said mobile wireless-communication optical-imaging device and wirelessly transmitting data derived from the medical image data and the subject's medical record identification from the mobile wireless-communication optical-imaging device to a second device separate from the mobile wireless-communication optical-imaging device.

BRIEF DESCRIPTION OF THE DRAWINGS

The foregoing will be apparent from the following detailed description, as illustrated in the accompanying drawings, in which.

DETAILED DESCRIPTION

Figure 1:
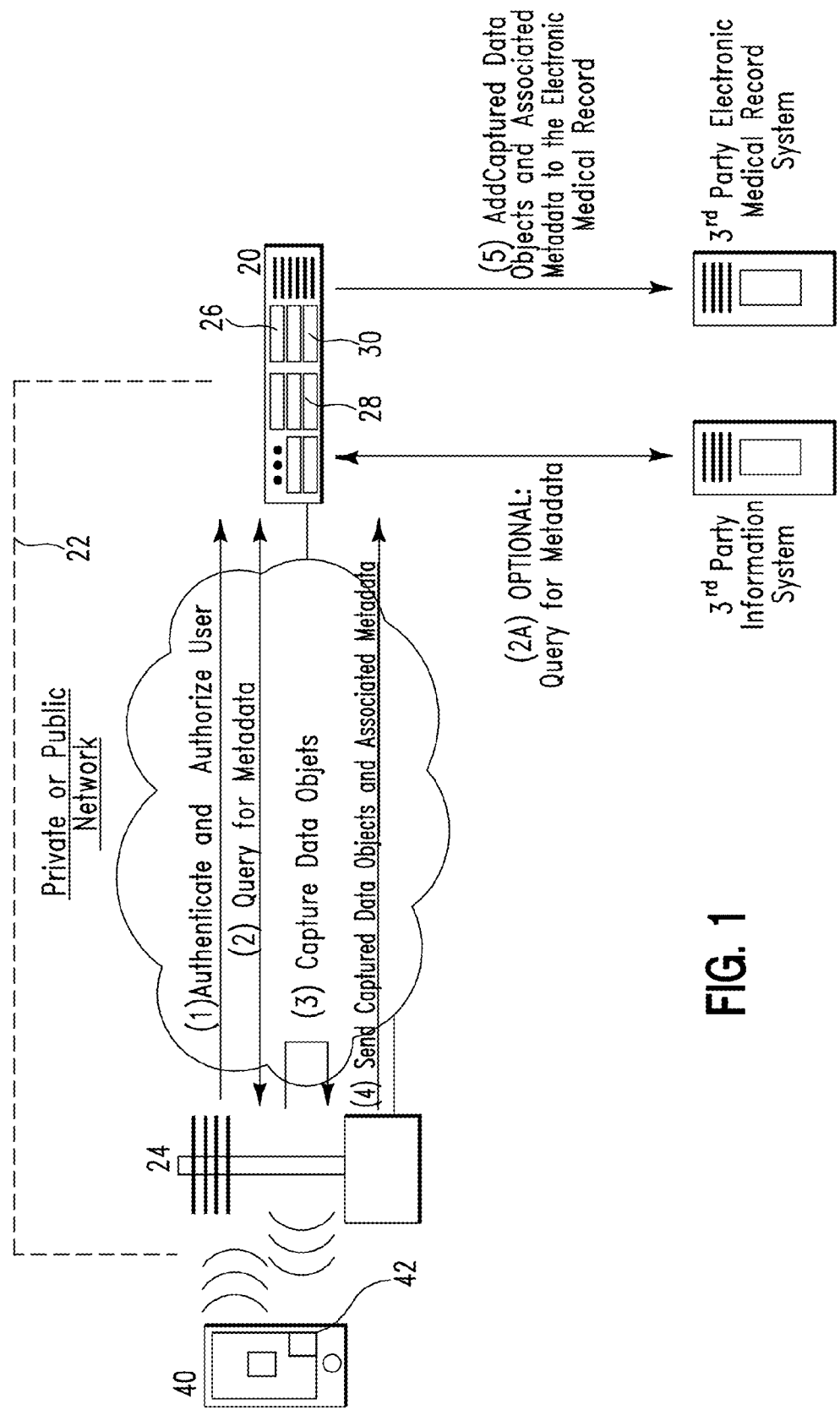
FIG. 1 is a block diagram illustrating one embodiment of a system that includes a handheld mobile wireless-communications optical-imaging device in communication with a server that includes a medical record database.

One embodiment of the present patent application includes a program running on a mobile wireless-communications optical-imaging device to use the mobile device's optical-imaging component, such as its camera, to obtain and store image data of a medical condition of a subject in the medical record of the subject that exists in a medical record system. Under the program, the user provides identifying information about the subject regarding the medical image data, and the program associates the identifying information with the image data as metadata.

The subject identifying information may be a medical record identification number for that subject. Alternatively, the subject identifying information may be information about the subject, such as patient name, subject identification number, date of birth, gender, patient ID number, or a combination of such information, such as subject name and date of birth. The subject identifying information becomes uniquely identifying metadata that associates an image to a medical record within an electronic medical record system. The subject identifying information may be provided to the mobile wireless-communications optical-imaging device by key pad entry, dictation, or selection from a list.

The mobile device then uses its wireless-communications component, such as its cell phone, wife, Bluetooth, or near field communication to transmit the image data along with the subject identifying information for recording in the subject's medical record on a server. The server may be part of the medical record system. As used in this patent application, a mobile wireless-communications optical-imaging device includes such handheld devices as a smart phone, a tablet or a phablet device.

While the present patent application is primarily about human patients, the medical provider can also be a veterinarian or horticulturalist, and the subject may be an animal or plant that has a secure medical record.

A subject's electronic medical record is a digital record of medical procedures and information associated with the subject. It is stored electronically and may be called up for viewing such as for a clinical review. An electronic medical record may include imaging results, lab results, a list of medications being taken, surgeries, medical devices, allergies, images, videos, procedures, evaluations, diagnosis, notes, and medical reports. Information is entered and stored for a subject over time that may extend for months and years. The data may include many different medical examinations, surgeries, and procedures.

Systems that include electronic medical records are regulated in many developed countries around the world to ensure that medical information associated with a subject is protected and provides a focus on quality and safety of the subject. Such regulations are provided by agencies including the FDA in the United States, TGA in Australia, Health Canada, National Health Service in the UK, EU Legislation in Europe. In many cases, these regulations determine how companies developing electronic medical records operate, including in areas including human resource procedures, product development, product implementation, service, support, and management procedures, among others.

Such systems in the US usually meet a standard for a registered medical device, as defined by FDA medical device regulation 21 CFR 807. Outside of the US, ISO 13485 defines the requirements of medical device organizations in countries and regions including Europe, Canada, Australia, Japan, and others.

One embodiment of the present patent application includes a user authentication and authorization before the program running on the mobile device allows the image data to be transmitted. In one alternative, the user authentication and authorization precedes the recording step in the subject's medical record on the server.

In one embodiment, the server includes a program to ensure that the image data is recorded in a format consistent with other records in the subject's medical record, such as DICOM.

In one alternative to storing the image data in the medical record itself, the image data of the medical condition is instead stored elsewhere, such as on a local server, and the medical record includes only a link to the image data so stored.

Medical imaging data includes still pictures and/or video. In one embodiment of the program designed and built by the present applicants, the user can take one or more pictures or videos. The program then allows the user to preview each of the pictures or videos and to select one, several, or all of them to be transmitted. During the send, the program allows the user to pause or cancel transmission. The program indicates the status of transmission of each medical image data object during its transmission. If transmission is successful, sending complete is indicated. If transmission fails transmission failed is indicated. A user may choose to resend failed or successfully sent data. Each item of medical image data is linked to the subject identifying information and medical procedure through metadata. The image, subject identifying information and any procedure metadata are all sent together in a single step using the http protocol. The program running on the mobile device uses the mobile device operating system to accomplish its workflow. Alternatively, the subject identifying information and any procedure information can be associated as image metadata after receipt in the server system.

In one embodiment, the mobile wireless-communications optical-imaging device is operated by a medical provider, such as a doctor, nurse, physical therapist, or other caregiver. The subject may be a patient of the medical provider. In another embodiment, the patient is authorized to operate the mobile wireless-communications optical-imaging device to record data objects about herself or himself.

In addition to image data objects that are received through its camera, such as still pictures and video, the mobile wireless-communications optical-imaging device can acquire and transmit other data objects, such as audio files, sensor data, or any other kind of data that is received by the mobile wireless-communications optical-imaging device. Such data objects can be received through its microphone or through another input device, such as a keyboard or a touch screen. Such data objects can also be received through another sensor that is integral with the mobile wireless-communications optical-imaging device, such as its accelerometer, angular rate sensor, or GPS. Such data objects can also be received through a sensor connected to the mobile wireless-communications optical-imaging device, such as a temperature sensor, a pressure sensor, a chemical sensor, or a location sensor. The mobile wireless-communications optical-imaging device may also include other input-output devices, such as a speaker and a display.

In one embodiment the subject identifying information and the procedure are input by the user typing an identification, such as a subject name or record number on the keyboard or touch screen of the input device. The subject identifying information can also be scanned in from a bar code QR code, or subject name or number on a subject's bracelet or other identification source using the mobile wireless-communications optical-imaging device. The subject identifying information and procedure can also be highlighted and selected by the user from a list of subject identifying information, such as patient names and dates of birth that the program provides to the user on the mobile wireless-communications optical-imaging device. The list that appears on the mobile wireless-communications optical-imaging device may contain, for example, those subjects that have appointments that day.

In one embodiment, the user wirelessly transmits a query from the mobile wireless-communications optical-imaging device to a third-party device to obtain a list of subject identifying information. In the case when subject identifying information is returned to the mobile wireless-communications optical-imaging device for multiple subjects, the user selects the specific subject from the list and that subject identifying information is associated with the medical image data objects transmitted.

In one embodiment, the mobile wireless-communications optical-imaging device acquires medical image data related to the subject and the subject identifying information and assigns the subject identifying information to the medical image data. The mobile wireless-communications optical-imaging device then wirelessly transmits both to a device to display, communicate, and/or store health care information and/or to a device used for diagnosis, prevention, and/or treatment. In one alternative, the image can later be transmitted back to the mobile device for viewing on the mobile device In one embodiment, server 20 is part of wireless communications digital server system 22, as shown in FIG. 1. Wireless communications digital server system 22 includes wireless communications device 24 that wirelessly receives digital data from and transmits digital data to mobile wireless-communications optical-imaging device 40. Communications device 24 portion of wireless communications digital server system 22 also wired or wirelessly receives digital data from and transmits digital data to server 20. In one embodiment, wireless communications device 24 is mounted on a cell phone tower.

Server 20 includes processor 26 and storage device 28. In one embodiment wireless communications digital server system 22 includes medical record data base 30 that includes a medical record of the subject. In another embodiment, wireless communications digital server system 22 is connected to another server that holds the medical record data base. The medical record data base may include medical records for multiple subjects. Typically each subject has a unique medical record identification number. The particular medical record for a specific subject is accessed for viewing or for storing additional data objects based on this unique medical record identification number.

Mobile wireless-communications optical-imaging device 40 also includes memory 42 connected for recording images and other data objects about the subject, such as audio data, and for acquiring subject identifying information.

In one embodiment, mobile wireless-communications optical-imaging device 40 runs an application program that directs the user to provide subject identifying information, such as a subject identification number, a subject name, and/or a subject date of birth. The application program may be stored on mobile wireless-communications optical-imaging device 40 or it may be stored on server system 22. The application program may also include provision for acquiring the date and time and for entry of data objects. The application program may also include provision for acquiring further identifying information, such as the specific body part being imaged or the specific body part that is the subject of another data object, test, procedure, order, exam, or encounter followed, the date and time of the photograph, a title or other identifier for the specific image or other data object, and/or the particular mobile device that is the source of the acquired image or other data object. This further identifying information is "metadata" for storing in the subject's medical record along with the image or other data object collected by mobile wireless-communications optical-imaging device 40.

In another embodiment, mobile wireless-communications optical-imaging device automatically acquires metadata from a $3^{rd}$ party server based on the subject identifying information, such as the subject identification number, date and time of the procedure, procedure type, body part, and/or other attribute.

In one embodiment, the program running on the server, "the server application," maps metadata received from a $3^{rd}$ party vendor to a common language, such as DICOM, so information returned is then provided using the DICOM attribute names, even if the $3^{rd}$ party server coming from different $3^{rd}$ party vendors provides the information using different attribute names.

In addition to such previously determined metadata attributes, the server application allows the handheld mobile wireless-communications optical-imaging device to receive and associate any other attribute as metadata associated with the image data object or other data object. For example, an attribute can be a unique one generated on the fly by the doctor. If generated by the doctor and input using, for example the mobile wireless-communications optical-imaging device touch screen, this attribute can be transmitted to the server and then sent back to the mobile wireless-communications optical-imaging device to be an associated metadata attribute, and optionally all subsequent queries from the handheld mobile wireless-communications optical-imaging device would include the new attribute as metadata.

The server application allows the user to select metadata attributes of interest to be returned to the phone. A configuration screen provided on the server allows an administrator to state the metadata to be provided by the $3^{rd}$ party, query a source, get the metadata back on the mobile device, map the attribute names given by the $3^{rd}$ party to a common language, such as the DICOM attribute name, and configure for translation to XML, and for transmission over HTTP. Alternatively, a user configuration screen provided on the mobile device can allow the user to state the metadata to be provided by the $3^{rd}$ party, query a source, get the metadata back on the mobile device, map the attribute names given by the $3^{rd}$ party to a common language, such as the DICOM attribute name, translate to XML, and transmit over HTTP.

In one embodiment, the user operates mobile wireless-communications optical-imaging device 40 to acquire an image and/or another data object, for example by taking one or more pictures, a video, and/or an audio recording of a medical condition of the subject, such as a still photograph of a beauty mark, a wound, a rash, a varicose vein, or an inflamed region or a video of the subject limping, the range of motion of a joint, or evidence of abuse.

A data object can also be an audio file that includes a conversation with the subject or dictation by the medical provider. The data object can also include image or audio of a test undertaken by the medical provider, such as a video and audio file of a subject taking a number of deep breaths, coughing, or undergoing a sleep study. A data object can also include image or audio of a procedure undertaken by the medical provider, such as removal of a beauty mark and identification of the sample. A data object can also include audio recording of heart beat, breathing, blood flow, or joint motion. A data object can also include recorded data from another sensor that may be connected to mobile wireless-communications optical-imaging device 40, such as a temperature sensor or a pressure sensor for providing data about the subject, such as body temperature or blood pressure.

In one embodiment, data derived from the acquired image or other data object and the subject identifying information are transmitted by mobile wireless-communications optical-imaging device 40 and received in wireless communications digital server system 20. In one embodiment, this wireless transmission is by way of radio transmission, such as with a transceiver over a wireless network, such as wifi, or across a mobile data network hosted by a mobile phone provider. It may also include transmission through the internet, as shown in FIG. 1, using a secure web service protocol. The wireless network can be either a private network or a public network. Other transmission schemes can also be used, for example, wireless optical communication.

In one embodiment, data derived from acquired metadata and from acquired image data is automatically converted to a standard medical data format. Standard medical data formats include DICOM and XDS. A native format, such as JPEG, text, wmv or avi can also be used for medical records. Commercial information systems, such as Electronic Medical Record (EMR) System, Picture Archiving and Communication System (PACS), Medical Imaging Archive System, Vendor Neutral Archive System (VNA), Radiology Information System (RIS), Cardiovascular Information System (CVIS), and Lab Information System (LIS), communicate using one or another of these standard and native formats and using their own formats.

In one embodiment, the converting to a standard medical data format is accomplished in a processor that is part of wireless communications digital server system 20 after receipt of the transmission from mobile wireless-communications optical-imaging device 40. The converting to a standard medical data format may also be accomplished in a processor that is part of mobile wireless-communications optical-imaging device 40 before transmission. The converting is accomplished using software, such as Keystone Suite, available from Mach 7 Technologies, Colchester, Vt., and software available from Medical Connections Ltd., England & Wales, or from PACSGEAR, Pleasanton, Calif.

Thus, the present patent application allows images and other data objects relevant to a subject's condition to be acquired by mobile wireless-communications optical-imaging device 40 and stored in the subject's electronic medical record associated with the subject identifying information on server 20 in the digital format consistent with that of the subject's electronic medical record. Thus, the present patent application provides for recording of medical data through a mobile phone, a tablet computer, or a phablet, and for that data to be stored in a subject's particular medical record.

In one embodiment, the application program includes an authentication and authorization procedure. The authentication and authorization procedure maintains subject data security by verifying that the user properly has access to record data in the subject's medical record. Included in the authentication and authorization procedure may be authentication data, such as a user name and password for the user. As an alternative to inputting a user name and password for the user another authenticating scheme may be used, such as a user retina scan, a user fingerprint scan, a scan of a user identity badge facial recognition, voice recognition, gesture recognition, and pattern recognition.

In one embodiment, authenticating and authorizing a user of mobile wireless-communications optical-imaging device 40 includes inputting the authenticating data to mobile wireless-communications optical-imaging device 40 and transmitting the authenticating data to the wireless communications digital server system.

In one embodiment, the authentication and authorization procedure is fulfilled before the program allows initiating the query for metadata and the process of acquiring digital images for a subject/procedure. Other schemes are also possible. For example, permitting acquisition of digital images but only allowing transmitting, or only allowing receipt, or only allowing storage at the server after authentication and authorization are fulfilled.

In one embodiment, the wireless communications digital server system includes different authorization schemes for different people. For example, a lab technician may have access to the medical record solely for the purpose of adding data to the medical record. In another scheme, the system may authorize a user, for example, the subject, only to read data in the medical record. In another scheme, the system may allow a user, for example, a doctor, to both add data and read data in the medical record.

In one embodiment, metadata related to the subject is acquired from data stored in system memory. In another embodiment, the metadata is obtained from a $3^{rd}$ party information system, such as Electronic Medical Record (EMR) System, Picture Archiving and Communication System (PACS), Medical Imaging Archive System, Vendor Neutral Archive System (VNA), Radiology Information System (RIS), Cardiovascular Information System (CVIS), and Lab Information System (LIS), where it is retrieved from storage on a server. From such a $3^{rd}$ party information system, the metadata is accessed based on a subject identification number, procedure date and time, body part, or other attributes that identifies the subject. The server can provide a list of subjects, one of which is selected by the user. In one embodiment, mobile wireless-communications optical-imaging device 40 receives this metadata from the $3^{rd}$ party information system. The mobile wireless-communications optical-imaging device 40 then transmits this metadata along with a data object to the server.

In one embodiment a plurality of data objects related to the subject are recorded with mobile wireless-communications optical-imaging device 40. Image data can include one or more still pictures and/or video of a medical condition, test, or procedure. Audio data can include recording of sounds, such as from voice or dictation. Audio data can also include recording of subject produced sounds from heart, breath, cough, and/or motion of a joint.

In one embodiment, voice and dictation are automatically transcribed into text. This transcribing may be accomplished either on the mobile device or on the server.

In one embodiment, mobile wireless-communications optical-imaging device 40 further includes a data input component, and the memory is connected for recording a data object provided by this data input. The data input component can be a data entry key pad and/or a touch screen. Thus, a typed note, a hand scribed note, and/or a hand drawn depiction can be input as a data object.

The term "modality" has been used to refer to various devices that can acquire a medical image. Modalities have included such medical devices as CT, MRI, X-ray, and ultrasound scanners. These modalities have been connected for communicating the medical images they acquired to an imaging system, such as a viewer, an archive, and/or an electronic medical record. An archive is a system that stores a record in digital format. A medical image stored in an archive may later be recalled for viewing by a user. The archive can be arranged to store the records in a data base in which all records of a particular subject are associated with an identification number for that particular subject. The present application allows a device such as a smart phone, a tablet computer, or phablet to become a modality that can acquire medical image data and wirelessly communicate that image data to a medical record.

Figure 2B:
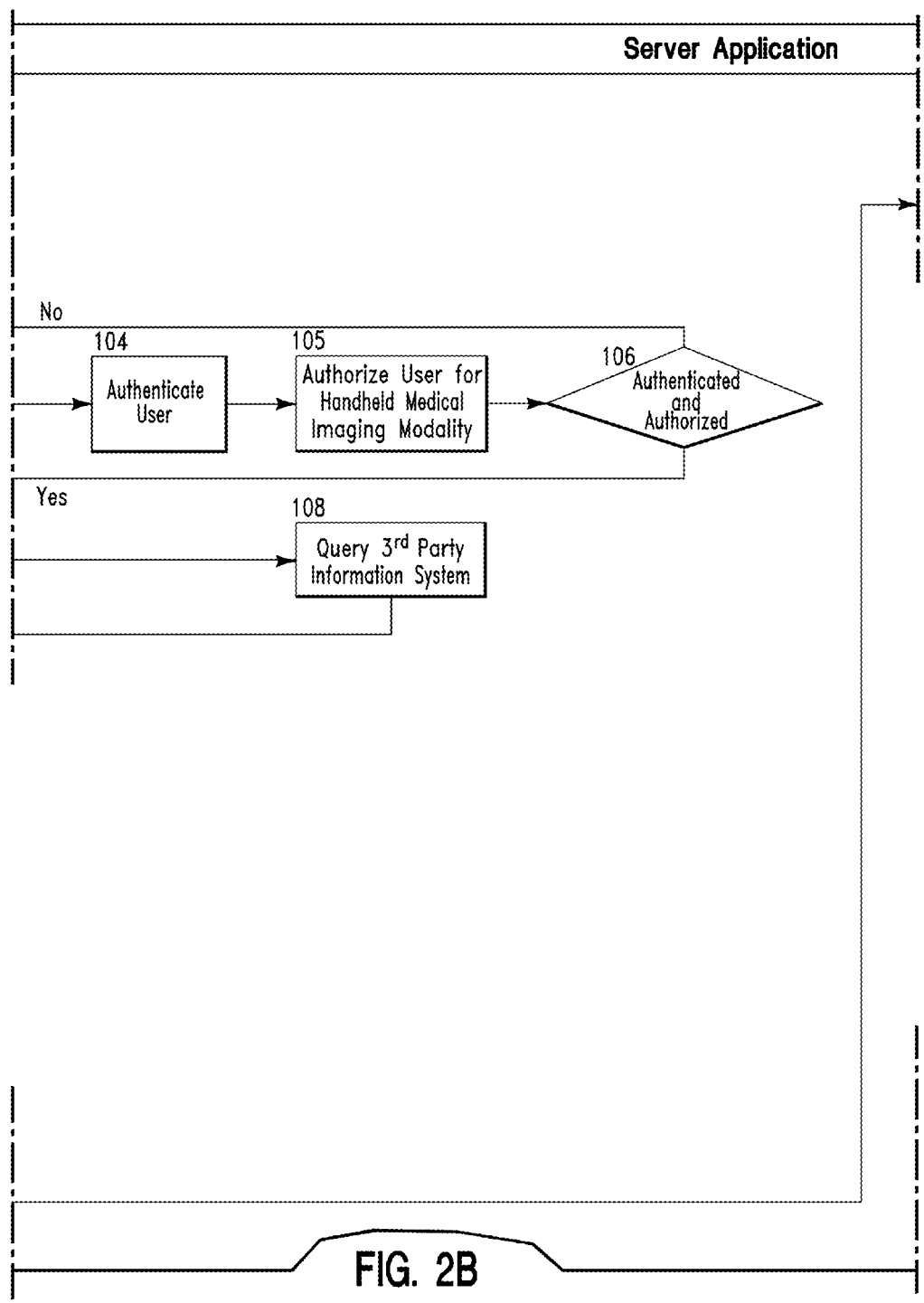
FIG. 2 is a flow chart illustrating one embodiment of programs that run on the handheld mobile wireless-communications optical-imaging device and on the server.
Figure 2C:
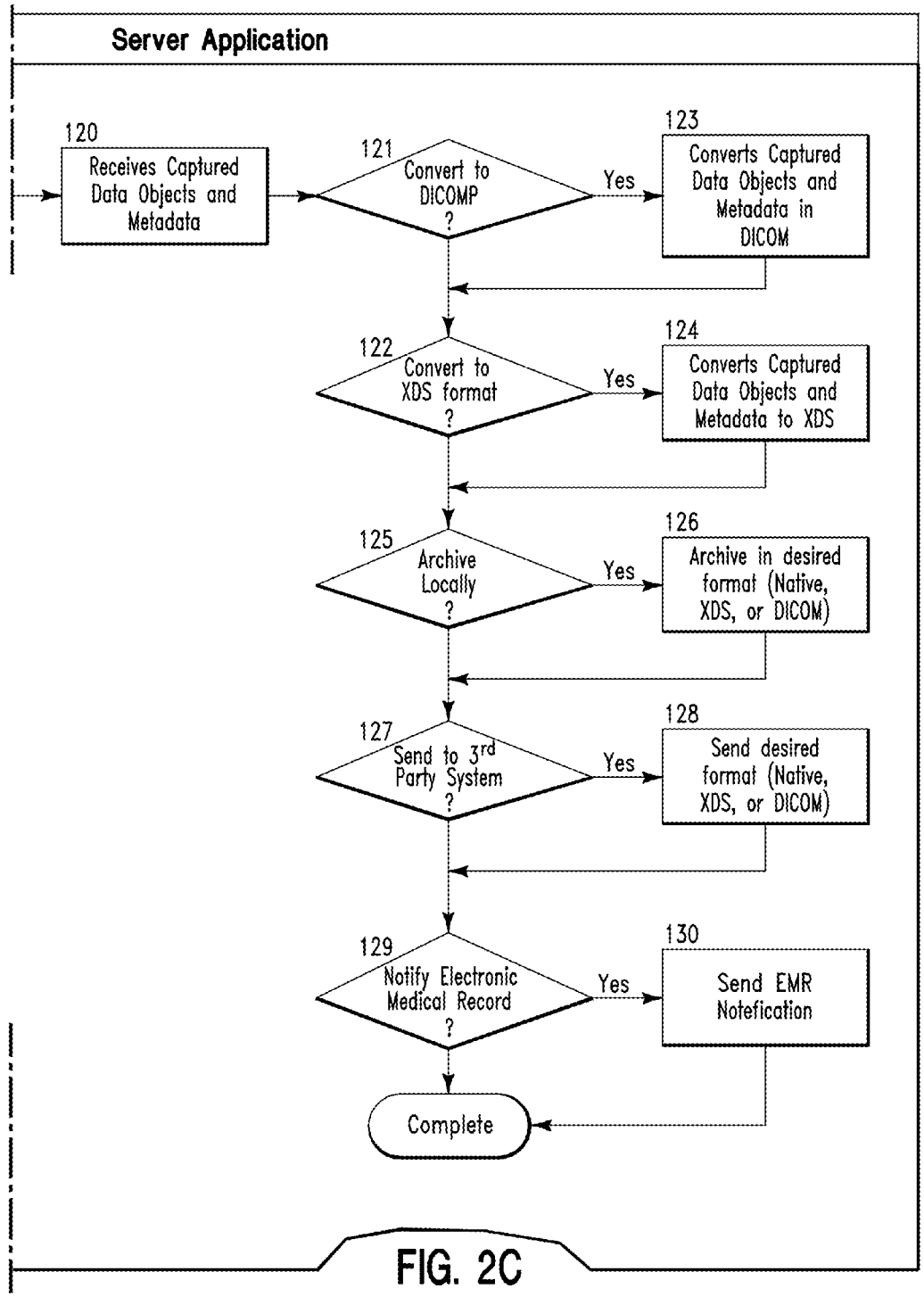

One embodiment is illustrated by the flow chart in FIG. 2 that depicts the operation of software that can run on mobile wireless-communications optical-imaging device 40 and/or on the wireless communications digital server system to enable medical images and other data objects captured in mobile wireless-communications optical-imaging device 40 to be transmitted and ultimately communicated to or linked from the electronic medical record of the subject. In FIG. 2 work flow conducted on the mobile device is indicate on the left while work flow conducted on the server is indicated on the right.

A user launches the client application on mobile wireless-communications optical-imaging device 40, as shown in box 100 of FIG. 2.

The client application checks whether the client application has been configured, as shown in decision box 101. If the client application has not been configured, the client application requests that the user configure the client application, including providing the server application url, as shown in box 102.

The user enters credentials on mobile wireless-communications optical-imaging device 40, including, for example user name and password, as shown in box 103 so the user can be authenticated and authorized to log into the server.

The client application contacts the server application over a secure web service protocol to authenticate and authorize the user based on the credentials entered, as shown in box 104.

The server application receives the request to authenticate that the user has a valid user name and password, as shown in box 105 and determines whether the user is authenticated and authorized as shown in box 106.

If the server application does not authenticate and authorize the user, the server application refuses and the client application returns the user to the user login screen, as indicated by the return arrow to box 103.

If the server application authenticates and authorizes the user, the client application initiates a query for subject identifying information and other metadata information, such as subject name, subject date of birth, subject identification number, order, exam, encounter, procedure, and order, as shown in box 107.

In one embodiment, the user selects a subject identifier and procedure from a list of subjects and procedures. The list can include such subject specific information as name, date of birth, subject identification number, medical record number (MRN), gender, age, type of procedure, allergies, and medications being taken. Alternatively, the user can type in or otherwise enter the subject identifying information. The user can also query the server to obtain information available from a $3^{rd}$ party information system, and the query is transmitted over a secure web service protocol to the application server and from there the query is directed to a $3^{rd}$ party information system to retrieve relevant additional metadata, as shown in box 108. In one embodiment, when the $3^{rd}$ party information system receives the query and transmits the relevant additional metadata to the application server, the application server then forwards the relevant metadata to the client application, as also shown in box 108.

The client application then presents the metadata information to the user and the user selects the metadata relevant to the subject, order, exam, encounter, procedure, and/or order being performed, as shown in box 109.

The user may choose whether to select to manually enter metadata or modify some of the returned metadata, as shown in the decision box 110 and the user can so modify, as shown in box 111. For example, the user can modify the date and time of the procedure or the body part examined.

The user may continue to capture data objects, as shown in box 112, such as still photos, videos, text notes, voice clips, audio files, dictations, transcribe notes through voice recognition, as shown in box 113. More than one data object of any type may be captured. The notes may, for example, be related to the photograph.

The user then selects the data object or objects to be sent to the server, as shown in box 114. This may include all of the captured data objects captured or a subset of those data objects.

The user then selects to have the selected captured data objects and metadata from the client application sent to the server application, as shown in box 115. In addition, the user has the option to cancel sending or to resend.

Figure 3:
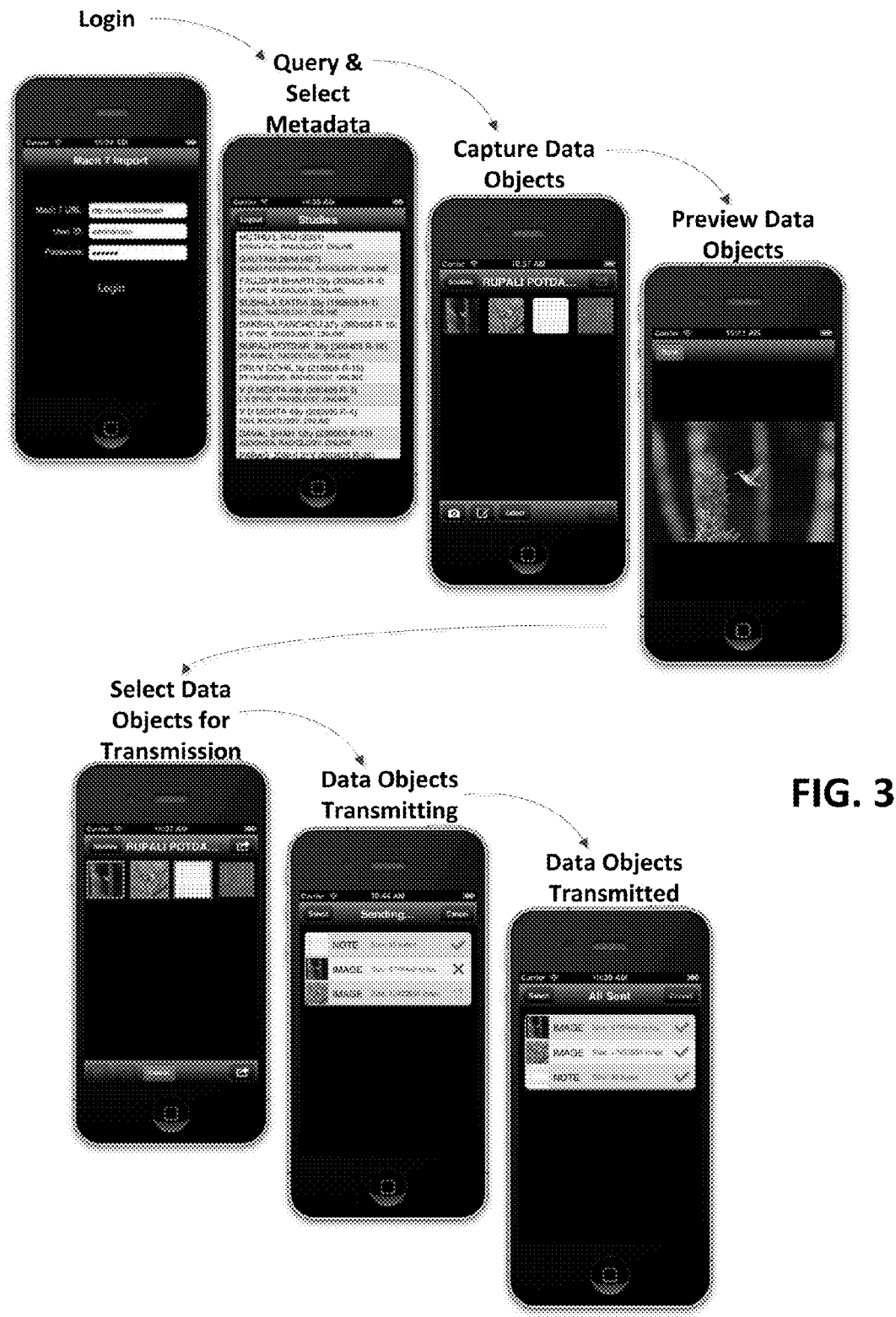
FIG. 3 is a sequence of views of a handheld mobile wireless-communications optical-imaging device illustrating steps of the program of FIG. 2, including login, identification of the subject, taking and previewing the image, selecting an image for transmission and transmitting the image.

Login, query and select metadata—including subject identifying information, capture data objects, preview data objects, select data objects for transmission, data objects transmitting, and data objects transmitted steps are also illustrated on a mobile phone in FIG. 3.

The client application may then display the status of the captured data objects and metadata being sent to the server application over a secure web service protocol.

The server application receives the captured data objects and metadata as shown in box 120, and audits the user and device from where the captured data object and metadata were acquired.

Action taken by the server application depends on how the server application has been configured. For example, the server application may consider whether to convert the captured data objects and metadata to a DICOM format, as shown in decision box 121, or to a cross document sharing (XDS) format, as shown in decision box 122. If configured to convert to DICOM, the application server does the conversion, as shown in box 123, and, if configured to convert to XDS, the application server does the conversion, as shown in box 124.

The server application then determines whether to locally archive the captured data objects in their DICOM, XDS, and/or original format, as shown in decision box 125. If configured to archive locally, the application server does the local archiving in the specified format, as shown in box 126.

The server application then determines whether to send the captured data objects in their DICOM, XDS, and/or original format to an external $3^{rd}$ party system, as shown in decision box 127. If configured to send to an external $3^{rd}$ party system the server application does so, as shown in box 128.

The server application then determines whether to notify the subject's electronic medical record of the captured data objects and metadata, as shown in decision box 129. If configured to so notify the server application does so, as shown in box 130. This notification includes either sending the captured data objects in the desired format to the electronic medical record or sending a link, such as a web url or xds location, to the electronic medical record indicating where the captured data objects may be reviewed.

While several embodiments, together with modifications thereof, have been described in detail herein and illustrated in the accompanying drawings, it will be evident that various further modifications are possible without departing from the scope of the invention as defined in the appended claims. Nothing in the above specification is intended to limit the invention more narrowly than the appended claims. The examples given are intended only to be illustrative rather than exclusive.

What is claimed is:

1. A method of acquiring medical image data of a first subject by a user, wherein the first subject is one of a plurality of different subjects, wherein each of the subjects has a distinct subject medical record on a server, wherein the medical image data for each subject is stored in the distinct subject medical record of that subject, comprising:
   a. providing a mobile wireless-communication optical-imaging device, wherein said mobile wireless-communication optical-imaging device includes an optical imaging component, an input component, a wireless two-way communication component, and a program, wherein said program includes authenticating the user, and wherein said program includes a request for subject identifying information;
   b. providing user authenticating data on said mobile wireless-communication optical-imaging device;
   c. wirelessly transmitting said user authenticating data with said wireless-communication optical-imaging device;
   d. capturing first medical image data related to the first subject with said mobile wireless-communication optical-imaging device, wherein said optical imaging component of said mobile wireless-communication optical-imaging device is operated by the user to capture said first medical image data;
   e. providing first subject identifying information on said mobile wireless-communication optical-imaging device in response to said request for subject identifying information, wherein said first subject identifying information uniquely identifies a first subject medical record, wherein the first subject is one of a plurality of subjects who may be selected by the user on said mobile wireless-communication optical-imaging device, wherein the user is different from the first subject, wherein the user, in selecting the first subject on said mobile wireless-communication optical-imaging device from the plurality of subjects who may be selected, provides said first subject identifying information; and
   f. wirelessly transmitting first data derived from said first medical image data together with said first subject identifying information from said mobile wireless-communication optical-imaging device to a second device for storage in said first subject medical record, wherein the second device is separate from said mobile wireless-communication optical-imaging device and is linked to a device that stores said first subject medical record, further comprising storing said data derived from said first medical image together with said first subject identifying information in said first subject medical record.

2. A method as recited in claim 1, wherein said program request to the user to provide said subject identifying information includes the program providing a list of the plurality of subjects who may be selected by the user, wherein the user can select the first subject from said list.

3. A method as recited in claim 1, wherein said program adds said first subject identifying information as first metadata with said first medical image data on said mobile wireless-communication optical-imaging device, and in said wirelessly transmitting (f), wirelessly transmitting said first metadata together with said first medical image data.

4. A method as recited in claim 1, wherein said program further includes authenticating the user before said providing said first subject identifying information in said program and said wirelessly transmitting said first data derived from said first medical image data together with said first subject identifying information.

5. A method as recited in claim 1, wherein said program runs on said mobile wireless-communication optical-imaging device.

6. A method as recited in claim 1, wherein said authenticating data includes at least one from the group consisting of a user name and a password, a fingerprint, a retinal scan, facial recognition, voice recognition, gesture recognition, and pattern recognition.

7. A method as recited in claim 1, further comprising accessing said first medical image data on said second device, wherein said accessing includes providing said first subject identifying information.

8. A method as recited in claim 1, wherein said second device includes a storage medium.

9. A method as recited in claim 8, wherein said storage medium stores said first subject medical record, further comprising storing said first data derived from said first medical image data together with said first subject identifying information in said first subject medical record.

10. A method as recited in claim 1, wherein said mobile wireless-communication optical-imaging device further includes at least one from the group consisting of a speaker and a microphone.

11. A method as recited in claim 10, further comprising acquiring audio data with said mobile wireless-communication optical-imaging device, wherein said acquiring audio data includes recording said audio data in an audio file, associating said first subject identifying information to said audio file with said program on said mobile wireless-communication optical-imaging device, and transmitting data derived from said association to said second device.

12. A method as recited in claim 11, wherein said audio file includes a recording of sound from of at least one from the group consisting of voice, dictation, heart, breath, cough, blood flow, and motion of a joint.

13. A method as recited in claim 12, further comprising automatically transcribing said dictation.

14. A method as recited in claim 1, wherein said mobile wireless-communications optical-imaging device further includes a memory, wherein said memory is connected for recording a data object based on data input through said input component.

15. A method as recited in claim 14, wherein said input component includes at least one from the group consisting of a key pad, a touch screen, a microphone for voice recognition, a mouse, a touch pad, and an optical motion sensor for gesture recognition.

16. A method as recited in claim 14, wherein said data object includes at least one from the group consisting of a typed note, a hand scribed note, and a hand drawn depiction.

17. A method as recited in claim 1, further comprising acquiring first metadata with said mobile wireless-communication optical-imaging device and transmitting data derived from said first medical image data together with said first metadata and said first subject identifying information from said mobile wireless-communication optical-imaging device to said second device.

18. A method as recited in claim 17, wherein said acquiring first metadata includes acquiring metadata from a $3^{rd}$ party information system based on providing the $3^{rd}$ party information system with said first subject identifying information or a procedure.

19. A method as recited in claim 18, further comprising selecting relevant metadata from information provided by the 3rd party information system with said mobile wireless-communication optical-imaging device.

20. A method as recited in claim 19, wherein said metadata includes at least one from the group consisting of a subject identification number, a subject medical record identification number, a subject name, an order, an exam, an encounter date, a procedure, a modality type, a body part, a source of a captured data object, and a time of a captured data object.

21. A method as recited in claim 1, wherein said mobile wireless-communications optical-imaging device includes at least one from the group consisting of a mobile smart phone, a tablet device, and a phablet.

22. A method as recited in claim 1, wherein said wirelessly transmitting includes at least one secure protocol from the group consisting of mobile phone, private network, public network, and Bluetooth.

23. A method as recited in claim 1, wherein said input component includes a microphone, further comprising acquiring a plurality of data objects related to the first subject with said mobile wireless-communications optical-imaging device, wherein said data objects include at least one from the group consisting of optical imaging component acquired data, microphone acquired data, and input component acquired data.

24. A method as recited in claim 1, wherein said medical image data includes at least one from the group consisting of a still picture and a video.

25. A method as recited in claim 1, further comprising automatically converting said medical image data to a standard medical data format.

26. A method as recited in claim 25, wherein said standard medical data format includes one from the group consisting of DICOM and XDS.

27. A method as recited in claim 25, further comprising storing said data derived from said first subject medical image data and said first subject identifying information in said standard medical format in at least one from the group consisting of said first subject medical record and a location accessible from said first subject medical record.

28. A method as recited in claim 1, wherein said request includes a request to enter said subject identifying information with said input component.

29. A method as recited in claim 28, wherein said entering said subject identifying information with said input component includes at least one from the group consisting of typing and scanning.

30. A method as recited in claim 1, wherein said program includes a request for authenticating the user.

* * * * *